United States Patent
Fais et al.

(10) Patent No.: US 8,617,806 B2
(45) Date of Patent: Dec. 31, 2013

(54) METHOD TO MEASURE AND CHARACTERIZE MICROVESICLES IN THE HUMAN BODY FLUIDS

(75) Inventors: Stefano Fais, Rome (IT); Mariantonia Logozzi, Rome (IT)

(73) Assignee: Hansabiomed OU, Tallinn (EE)

( * ) Notice: Subject to any disclaimer, the term of this patent is extended or adjusted under 35 U.S.C. 154(b) by 417 days.

(21) Appl. No.: 12/321,412

(22) Filed: Jan. 21, 2009

(65) Prior Publication Data

US 2009/0220944 A1    Sep. 3, 2009

Related U.S. Application Data

(60) Provisional application No. 61/062,528, filed on Jan. 25, 2008.

(51) Int. Cl.
*G01N 33/53*        (2006.01)

(52) U.S. Cl.
USPC .................................. 435/5; 435/7.1

(58) Field of Classification Search
None
See application file for complete search history.

(56) References Cited

U.S. PATENT DOCUMENTS 6,812,023 B1 * 11/2004 Lamparski et al. ........... 435/325
2012/0058492 A1 * 3/2012 Lozupone et al. ........... 435/7.23

FOREIGN PATENT DOCUMENTS

WO      WO03/063690      8/2003

OTHER PUBLICATIONS

Pisitkun et al. Identification and proteomic profiling of exosomes in human urine, PNAS, vol. 101, No. 36, pp. 13368-13373, Sep. 7, 2004.*
Liu et al. Murine Mammary Carcinoma Exosomes Promote Tumor Growth by Suppression of NK Cell Function. J. of Immunology, 2006, 176: 1375-1385.*
Choi et al. Proteomic Analysis of Microvesicles Derived from Human Colorectal Cancer Cells. J. Proteome Res., 2007, 6 (12), pp. 4646-4655.*
Thery et al. Exosomes: composition, biogenesis and function. Nat Rev Immunol. Aug. 2002;2(8):569-79.*
http://www.biology-online.org/dictionary/Housekeeping_protein for definition online.*
Admyre, C. et al. 2008. Exosomes—nanovesicles with possible roles in allergic inflammation. Allergy 63: 404-408.
Aoki, N. et al. 2007. Identification and characterizationof microvesicles . . . Endocrinology 148:3850-3862.
Koga, K. et al 2005. Purification, characterization and biological significance . . . Anticancer Research 25: 3703-3708.

* cited by examiner

*Primary Examiner* — Michelle S Horning
(74) *Attorney, Agent, or Firm* — Gearhart Law, LLC (57) ABSTRACT

This disclosure provides a method to capture, detect, characterize and quantify human exosomes in small volumes of human body fluids by using a sandwich ELISA test. This method allows a full characterization of an exosome preparation, thus providing a tool to distinguish a disease-related condition from a healthy state, by the use of a non-invasive assay. In fact, this method may be useful in screening, diagnosis and prognosis of tumors, with a simple plasma sample. At the same time measurement of circulating exosomes may provide information on the level of tumor mass present in a patient. The method provided here is suitable to evaluate presence of some infectious and/or transmissible agents, such as viral proteins or prion proteins, within circulating exosomes.

15 Claims, 6 Drawing Sheets

METHOD TO MEASURE AND CHARACTERIZE MICROVESICLES IN THE HUMAN BODY FLUIDS

PRIORITY

This application claims priority of the U.S. provisional application No. 61/062,528 filed on Jan. 25, 2008

FIELD OF THE INVENTION

The present invention relates generally to the field of cancer diagnosis. More specifically, the invention relates to a method to quantify and qualify exosomes in the human body fluids.

BACKGROUND

Exosomes are microvesicles of a size ranging between 30-120 nm, actively secreted through an exocytosis pathway normally used for receptor discharge and intercellular crosstalk. Exosomes may be detected in cell culture supernatants and some body fluids, following multistep ultracentrifugation. In addition to major hisotcompatibility complex proteins (MHCI, MHC II) and proteins involved in antigen presentation, exosomes may carry membrane and cytocolic proteins involved in many cellular functions. Exosomes are secreted under specific physiological conditions from different cell types such as dendritic cells (DC), lymphocytes, mast cells and epithelical cells. This process leads to the formation of basket-like cellular reservoirs that contain these multifusion-derived microvesicles, also called Multivesicular Bodies (MVB). This process has been resolved through utrastructure observations, particularly in normal cells. However, through immunoelectron microscopy and western blot analysis of exosome preparations it has been shown that these microvesicles co-express markers of different intracellular vacuoles, such as early endosomes (e.g. Rab5), lysosomes (e.g. CD63, CD81, LAMP-1) and late phagosomes (Rab7), but also some other more cell-specific proteins (e.g. MHC class III antigens).

Release of exosomes from tumor cells is dramatically higher than from normal cells, and it is often associated with immunosuppressive effects. Tumor derived exosomes are in many aspects comparable to the exosomes of normal cells, except for the expression of some tumor markers, such as CEA for colonic carcinoma, MART-1 or gp-100 for melanoma. Moreover, the origin of tumor exosomes seems to be in many aspects dissimilar to that of normal exosomes. This is probably because malignant cells have more dynamic vesicle traffic from the cytoplasm to the extracellular space and vice versa.

The role of tumor exosomes in cancer progression is a recently emerged reserach area. Inital data suggests that these organelles act as carriers of tumor antigenic material for DC-mediated T cell crosspiming. Such results give support to clinical attempts to use tumor exosomes as anti-cancer vaccines. Growing evidence concerning a vast array of suppressive effects exerted by these microvesicles on different components of the immune system is clearly supporting the involvement of tumor exosomes in disease progression. In particular, it has been recently shown that exosomes secreted by human tumor cells of various origins are able to induce apotposis in activated T cells, through the expression of death ligands (e.g. FasL, TRAIL), inhibit NK functions and promote the generation of myeloid-derived suppressor cells from normal monocytes. These data, together with the reproducible evidence that exosomes of likely tumor origin can be abundantly found in plasma and nonplastic effusions of cancer patients, support a role of tumor exosomes in molding host microenvironment to allow tumor cells growth and progressions.

Given the increasing understanding of the role of exosomes in cancer progression and the fact that there is an increasing need to find new cures, improve diagnostics and follow up of malignancy and growth of tumors, there is accordingly a need for methods and tools to detect and measure exosomes in human fluids. The fact however is, that methods that are currently used to detect exosomes are either not quantitative (TEM) or only poorly quantitative (WB). Although flow cytometry has been used to quantify exosomes, this method does not allow a precise measurement that the researchers need. In fact, while FACS (Fluorescence Activated Cell Sorter) analysis is a suitable method to quantify cells, even of small size, but it is not suitable to quantify the amount of such small vesicles (i.e. 50-100 nm). Moreover, the rough measurement of total mean fluorescence does not allow a precise quantification on how many microvesicles are present in the given sample. Furthermore, FACS analysis does not allow simultaneous analysis of different samples. Therefore, there is a need for a method to detect and quantify exosomes from small amounts of body fluids. Moreover, given the fact that early diagnosis of cancer is essential for disease treatment, there is a need for potential tumor markers and prognostic factors.

SUMMARY OF THE INVENTION

A central problem in obtaining useful in vivo data on exosomes is the low level of efficiency of currently available methods to obtain exosomes in order to quantify and characterize them from human body fluids, particularly from plasma. The body fluids may also be ascite, cerebral fluids, bone marrow, urine, faeces or bronco-alveolar washing. To provide a solution to these currently faced problems, this disclosure provides a simple a reliable method to detect and quantify exosomes from body fluids, especially from human plasma. According to this disclosure an ELISA based test (called ExoTest) allows quantification and characterization of exosomes from human plasma of both healthy donors and tumor patients. Through this test characterization of exosome-like microvesicles from plasma of both SCID mice engrafted with human melanoma or colon carcinoma cells and tumors patients is possible. This disclosure shows that plasmatic levels of exosomes are directly related to the tumor size and caveolin-1 is exclusively detectable from exosomes purified from plasma of tumor patients. According to this disclosure detection of tumor exosomes in plasma of human patients is useful in diagnosis and follow up of human tumor malignancies.

The technology disclosed here allows a non-invasive test useful in clinical practice for diagnosis, follow up and screening of tumors. The technology according to this disclosure may also be used in clinical research of tumors. Moreover, as it is known that some viruses (e.g. HIV and HCV) as well as prions can be detected within exosomes released by cells or in plasma, the technology of this disclosure may be also used to characterisation and research of other diseases, such as viral, transmissible and autoimmune diseases. Moreover, this invention provides tools to improve existing clinical tests based on proteins that are expressed on exosomes (e.g. tumor markers, viral proteins, prion proteins).

The rationale of this invention is based on two key points:

1. There is no previous art on a method that allows quantification and characterization of exosomes, particularly in small volumes, often available in human plasma samples.

2. There is an unmet need of a non-invasive diagnostic and/or prognostic test in many human disease conditions, particularly in cancers.

Accordingly, an object of this invention is to provide a method to quantify and characterize exosomes, particularly in small volumes.

Another object of this invention is to provide a method to quantify and characterize exosomes in plasma samples.

Yet another object of this invention is to provide a method to measure exosome levels in less than 2 ml of body fluids, together with a mostly complete characterization of the protein composition of exosomes.

Moreover, an object of this invention is to provide a method to simultaneously quantify exosomes in several samples.

Furthermore, the test according to this disclosure shows that the quantity of exosomes in plasma is related to the size of the tumor. Accordingly another object of the invention is to provide a method to follow up and provide a prognosis of cancer patients.

Even further, an object of the invention is to provide a test to establish the cellular source of plasmatic exosomes and to evaluate presence of some infectious (HIV, HCV) and/or transmissible agent (e.g. prion proteins) within them.

BRIEF DESCRIPTION OF THE DRAWINGS

Exosomes purified from plasma of healthy donors and melanoma patients were quantified by ExoTest using CD63 (A) or caveolin-1(B) as detection antigens. Data is expressed as box plot representation: the horizontal and vertical lines in each box represent the median and the $25^{th}$-$75^{th}$ percentiles, respectively. Black dots represent outlier values. Exosome levels are expressed as OD450×10000. Differences between groups were evaluated by Mann-Whitney test.

Exosomes purified from plasma of melanoma patients (MEL) and healthy donors (HD) were quantified by ExoTest using as detection antigens CD63 or typical melanoma proteins such as gp100 and MART-1. Data are expressed as means±SD. Exosomes levels are expressed as OD450×1000.

DETAILED DESCRIPTION OF THE INVENTION

Exosomes are microvesicles of a size ranging between 30-120 nm, actively secreted in the extracellular environment by normal as well as tumor cells. Given the increasing understanding of the role of exosomes in cancer progression and the fact that there is an increasing need to find new cures, improve diagnostics and follow up of malignancy and growth of tumors, there is accordingly a need for methods and tools to detect and measure exosomes in human fluids. Because of the potential involvement of exosomes in promoting disease progression through a series of detrimental effects on tumor microenvironment, the possibility of quantifying exosomes in human plasma or serum, through a sensitive, specific and feasible assay is becoming a crucial issue. If such an assay would be available, it could become a fundamental tool for assessing the potential role of these microvesicles in cancer prognosis and as a novel prognostic factor or a marker for detecting or monitoring neoplastic disease. The currently used methods, e.g. TEM and WB, however are not quantitative or are only poorly quantititative, whereby there is a clear need for a method to detect and measure exosomes quantitatively in human fluids. Therefore the goal of this disclosure is to provide a new tool for clinical oncologists for diagnosing and follow up studies of cancer patients. Furthermore, a goal of this disclosure is to provide a novel method to be used to diagnose other human diseases, such as viral or prion diseases, where particles are transmitted in microvesicles.

The novel quantitative test that is disclosed here is based on ELISA mediated detection of exosomes and it is the first easy, sensitive and reliable test for quantifying exosomes. The proteins that are detected by this method are not exosome specific but are exclusively shared with cytoplasmic organelles such as endosomes and lysosomes, whose membranes are not recycled as for plasma membrane structures. This feature excludes the possibility of detecting these proteins on debris derived from necrotic tumor cells, or in their soluble form.

The assay of this disclosure preferably includes a universal tumor marker (caveolin1) which allows preferential detection of tumor-secreted exosomes. A series of comprehensive studies performed by different comparative methods (Western blotting and flow cytometry) and different experimental conditions described below in the examples, prove the reliability of the novel test of this disclosure.

The novel method of this disclosure is based on sandwich ELISA test that we call ExoTest, to capture and quantify plasmatic exosomes based on expression of housekeeping proteins (CD63 and Rab-5) and tumor-associated marker caveolin-1. ExoTest uses an anti-Rab5 antibody for capturing exosomes present in purified exosome preparations. As detecting antibody, ExoTest uses an antibody recognizing either an exosome antigen (CD63) or other antigens expressed by the cellular source of exosomes like caveolin-1, a protein associated to metastatic behavior of tumors. In a first set of experiments, we used exosome preparation from culture media of human tumor cell lines, comparing the results of ExoTest with those obtained by western blot and FACS. The results showed that typical exosomal antigens were detectable in exosome preparations by using all three methods. However, ExoTest allowed a quantitative analysis of exosomes and a wider panel of proteins in the same preparation with smaller amounts of starting material as compared to FACS or WB analysis. This technical feature is of paramount importance when the analysis is performed on plasma samples. Indeed, the analysis of plasma pools of SCID mice engrafted with human melanoma or colon carcinoma cells was often not reproducible or at least very difficult when WB was used while ExoTest allowed a quantitative analysis of exosome levels in the plasma of human tumor-SCID mice. A novel and important finding is that based on ExoTest results, exosome levels in the plasma are significantly correlated to the tumor size and increased with time after engraft. Moreover, circulating exosomes, together with the typical proteins, presented tumor markers expressed by the human tumors growing in the mice (not shown). Thus, ExoTest using the CD63 as detecting antigen was able to quantify exosomes in plasma of patients with melanoma and of healthy subjects. Since tumor cells secrete large amount of exosomes, we were actually surprised not to find a difference between the levels of CD63-positive exosomes in plasma of melanoma patients and healthy control persons. With the aim to identify possible tumor-specific exosomes, we performed ExoTest using caveolin-1 as detecting antigen. Recent publications have reported that the plasma levels of circulating caveolin-1 are significantly correlated with metastatic prostate adenocarcinoma. Interestingly, caveolin-1 has been implicated in the pathogenesis of oncogenic cell transformation, tumorigenesis, and metastasis. First, we demonstrated by FACS and WB that caveolin-1 is present on human tumor-derived exosomes, purified from plasma of tumor-engrafted SCID mice and tumor patients. Then, by using ExoTest we could observe a significant increase in the plasma levels of caveolin-1-positive exosomes in tumor patients as compared to plasma of healthy individuals, suggesting that caveolin-1 may represent a specific tumor marker, and that ExoTest is a successful test to quantify such increase.

Altogether, the results show that an exosome-detecting ExoTest is working and useful for detection and quantification of circulating exosomes in humans. Moreover, the test offers a possibility of detecting different proteins in plasma exosome preparations, with a potential application to specific type of tumor patients. This disclosure also provides a novel prognostic/diagnostic tool for tumor patients based on quantification and characterization of plasma exosomes. This is particularly relevant for melanoma patients, because sensitive and reliable serum markers are still limited and LDH (lactate dehydrogenase) levels remain the only prognostic serum factor for assessment of disease course and prognosis.

The invention is described in detail below. The examples and experimental details are disclosed to provide an improved understanding and guidance for those skilled in the art. The scope of the invention is determined by the appended claims.

Example 1

1. Sources of Exosomes

A. Cell Culture Supernatants

We used two types of human tumor cell lines, i.e. melanoma and colon carcinoma. Mel 501 and Mel BS are two metastatic melanoma cell lines obtained from melanoma lesions of patients, surgically resected (Istituto Nazionale dei Tumori, Milan, Italy). We also used two colorectal carcinoma cell lines Colo206 (generated from liver metastasis of colorectal cancer patient) and 1869 col (provided by Dr. Maccalli, Istituto Superiore di Sanita'). All cell lines were cultured in RPMI 1640 medium supplemented with 100 IU/ml penicillin, 100 μg/ml streptomycin (Gibco), 2 mM glutamine I(Gibco) and 10% fetal calf serum (FCS) (Invitrogen, Milan, Italy). Human monocytes-derived macrophages (MDM) were obtained from buffy coats of healthy blood donors using CD14 magnetic beads (Milteny Biotec, Germany) and GM-CSF (500 U/ml) for 5 days in culture.

B. Human Tumor SCID-Mouse Plasma

CB.17 SCID/SCID female mice (Harlan, S. Pietro al Natisone, Italy) were used at 4-5 weeks of age and were kept under specific pathogen-free conditions. All animal procedures were carried out according to UKCCR guidelines. SCID mice were housed in micro isolator cages and all food, water and bedding were autoclaved prior to use. Mice were injected subcutaneously into the right flank with $2.5 \times 10^6$ cells/mouse of human melanoma or colon carcinoma cells. Tumor growth was measured by a caliper and the tumor weight was estimated with the formula: Tumor weight (mg)=length (mm)× width$^2$ (mm)/2, as previously described (Luciani L et al., J. Natl. Cancer Inst., 2004). The engrafted tumors were allowed to grow up to a weight of 500 mg and 500 μl of plasma from tumor-engrafted mice were collected from different animals sacrificed at different time-points during tumor growth.

C. Human Donors and Tumor Patients' Plasma

Human plasma samples were collected from EDTA-treated whole blood from patients with primary or metastatic melanoma and from age and sex-matched healthy donors. Samples were stored at −70° C. until analysis.

2. In Vitro and In Vivo Exosome Preparations

Supernatants from human melanoma and colon carcinoma cell lines were harvested from 72 h confluent cell cultures in T-175 flasks and microvesicles were isolated as previously described (Andreola et al., J. Exp. Med. 2002) with minor modifications. Briefly, after centrifugation at 300×g for 10 minutes to pellet the cells, the supernatant was centrifuged at 1,200×g for 20 minutes followed by 10,000×g for 30 minutes. The supernatant was filtered by using a 0.22 μm filter (Stericup™, Millipore Corp., Bedford, Mass., USA) and then centrifuged at 100,000 g for 1 h in a Beckman ultracentrifuge (Beckman Coulter) in order to pellet exosomes. After one washing in a large volume of phosphate-buffered saline (PBS), exosomes were suspended in a small volume of PBS or in the proper lysis buffer, and stored at −80° C. for further experimental analysis.

In order to obtain exosomes from plasma samples, heparinized blood from SCID mice engrafted with human tumors or from tumor patients and healthy donors were centrifuged at 400×g for 20 minutes. Plasma was then collected, aliquoted and stored at −70° C. until analysis. Plasma samples were subjected to the same centrifugal procedure described above to isolate exosomes by using a Beckman TL100 for ultracentrifugation of small volumes.

3. Flow Cytometry Analysis of Exosomes

Determination of antigen expression on exosomes was performed by flow cytometry analysis on purified exosomes bound onto latex beads. Exosome preparations (5-10 µg) were incubated with 5 µl 4-µm-diameter aldehyde/sulfate latex beads (Interfacial Dynamics, Portland, Oreg.) and resuspended into 400 µl PBS containing 2% FCS. Exosomes-coated beads (20 µl) were incubated with the following antibodies: anti-Rab5 (Santa Cruz), anti-CD63-FITC (Pharmigen), anti-CD81-PE (Pharmingen), anti-cavelolin-1 (clone N-20, Santa Cruz) for 30 minutes at 4° C., followed, when needed, by incubation with PE- or FITC-conjugated secondary antibody and analyzed on a FACSCalibur flow cytometer (BD Biosciences).

4. Western Blot Analysis of Exosomes

Purified exosomes were lysed in lysis buffer containing 1% Triton X-100, 0.1% SDS, 0.1 M Tris HCl (pH 7) and protease inhibitors (10 µg/ml aprotinin, 10 µg/ml leupeptin and 2 mM phenylmethylsulfonyl fluoride) (Sigma). Exosome protein concentration was determined by Bradford microassay method (Bio-Rad Laboratories, Hercules, Calif.). A total of 50 µg of proteins were resuspended in SDS sample buffer, boiled for 5 min, separated on 10% SDS-PAGE gel and electroblotted on nitrocellulose (Protran BA85, Schleicher and Schuell). Membranes were blotted with antibodies to CD63 (diluted 1:50) and Rab-5b (diluted 1:50), incubated with appropriate HRP-conjugated secondary antibodies (Amersham Pharmacia) and visualised by enhanced chemiluminescence (ECL, Pierce).

5. Development of an ELISA Test for Exosomes (ExoTest)

The novel ELISA test (ExoTest) according to this disclosure is based on the presence of specific proteins in the exosomes. These proteins are shared with cytoplasmic organelles such as endosomes and lysosomes (Rab-5 and CD63, respectively), whose membranes are not shed or recycled as for plasma membrane structures, thus excluding the possible presence of structures deriving from membrane disruption.

Ninety-six well-plates (Nunc, Milan, Italy) were coated with polyclonal anti-Rab-5b antibody (clone A-20 Santa Cruz) in a volume of 100 µl/well of carbonate buffer pH 9.6 at the final concentration of 4 µg/ml and incubated overnight at 4° C. After 3 washes with PBS, 100 µl/well of blocking solution (PBS containing 0.5% BSA) was added and left at room temperature for 1 hour. Following three washes in PBS, 50 µg of purified exosomes (in a final volume of 100 µl/well) were added and incubated overnight at 37° C. After three washes with PBS, the appropriate detection antibody (anti-CD63 Mab (clone H5C6 Pharmingen) or anti-caveolin-1 Mab (clone 2297, Pharmingen)) was diluted at 4 µg/ml in blocking solution and 100 µl/well was incubated for 1 hour at 37° C. After three washes with PBS, the plate was incubated with 100 µl of HRP-conjugated anti-mouse-peroxidase secondary antibody (Pierce, Milan, Italy) diluted 1:50,000 in blocking solution for 1 hour at room temperature. After the final three washes with PBS, the reaction was developed with POD (Roche Applied Science, Milan, Italy), blocked with 1 N $H_2SO_4$ and optical densities were recorded with an ELISA reader by using a 450 nm filter (Biorad).

Example 2

Figure 1:
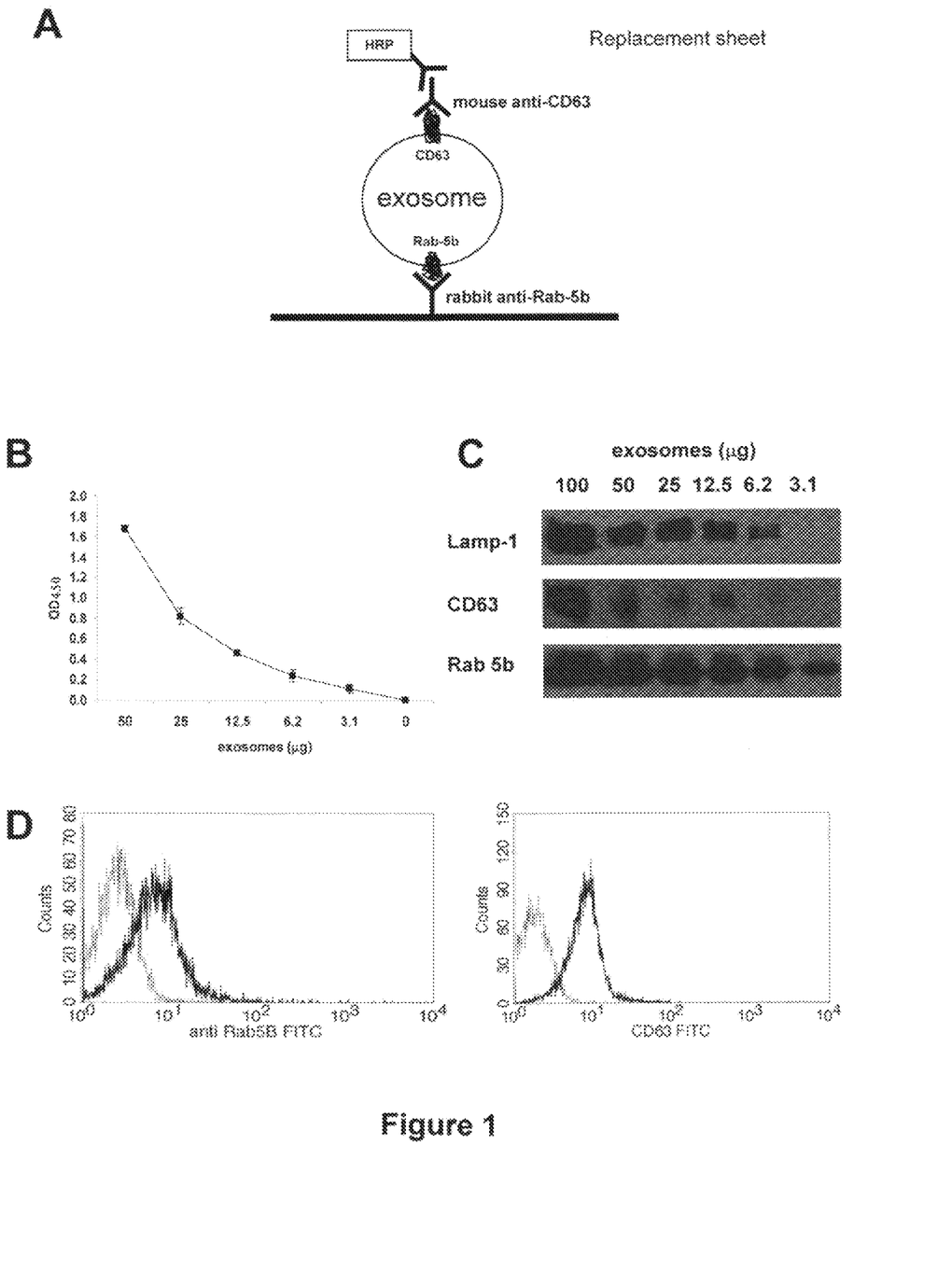
FIG. 1. Detection of Exosomes Purified from Cell Culture Supernatants of Human Melanoma
  A. Schematic representation of ExoTest (ELISA) set up for exosome detection and quantification.
  B. Dose-escalation analysis of purified CD63+ exosomes by ExoTest. The initial concentration corresponded to 50 μg of exosomes and exosomes were added in two-fold dilutions.
  C. Western blot analysis of CD63, Rab5b and Lamp-1 expression in different amounts of exosomes purified from culture supernatants of human melanoma cells (Me501)
  D. FACS analysis of Rab5b and CD63 expression on melanoma-derived exosomes purified from the supernatant Me501 cells and coated to latex beads.

ExoTest Provides Quantification of Exosomes Present in Cell Culture Preparations and has Higher Sensitivity for Exosome Protein Detection than Western Blot Analysis Culture supernatants of melanoma and colon carcinoma cell lines were processed following the standard procedure to obtain purified exosomes as described above. The sandwich ELISA set up to detect exosomes (ExoTest, see FIG. 1A) was performed on exosome preparations obtained from cell culture supernatants by differential centrifugation. ExoTest was able to provide a quantification of the exosomes present in the cell culture supernatants, being CD63+ exosomes detectable in dose-dependent manner (FIG. 1B). Negative controls, represented by fractions derived from pellet obtained after the 10 000 g centrifugation, exosomes purified from cell culture medium alone and by only secondary antibody resulted in a barely measurable optical density (OD=0.07+/−0.01). Intra- and inter-test variability were calculated on six replicates of the same preparation run on three different plates and were 30% and 35%, respectively.

Western blot and FACS analysis of the same purified exosome preparations confirmed the qualitative data obtained by ExoTest. In fact, Rab-5b, Lamp-1 and to a lesser extent CD63 proteins were detectable in the various exosome preparations both by WB in exosome lysates (FIG. 1C) and both Rab-5b and CD63 were detected by FACS on exosomes bound to latex beads (FIG. 1D). However, exosome detection and quantification by ExoTest showed a higher sensitivity for the detection of CD63 protein with respect to WB analysis (FIG. 1C). Indeed, while at least 12.5 µg of exosomal proteins were needed to properly detect either CD63 or Rab-5b by WB, ExoTest was able to clearly detect exosomes starting from a minimum amount of 3 µg of purified exosome preparations.

Example 3

Figure 2:
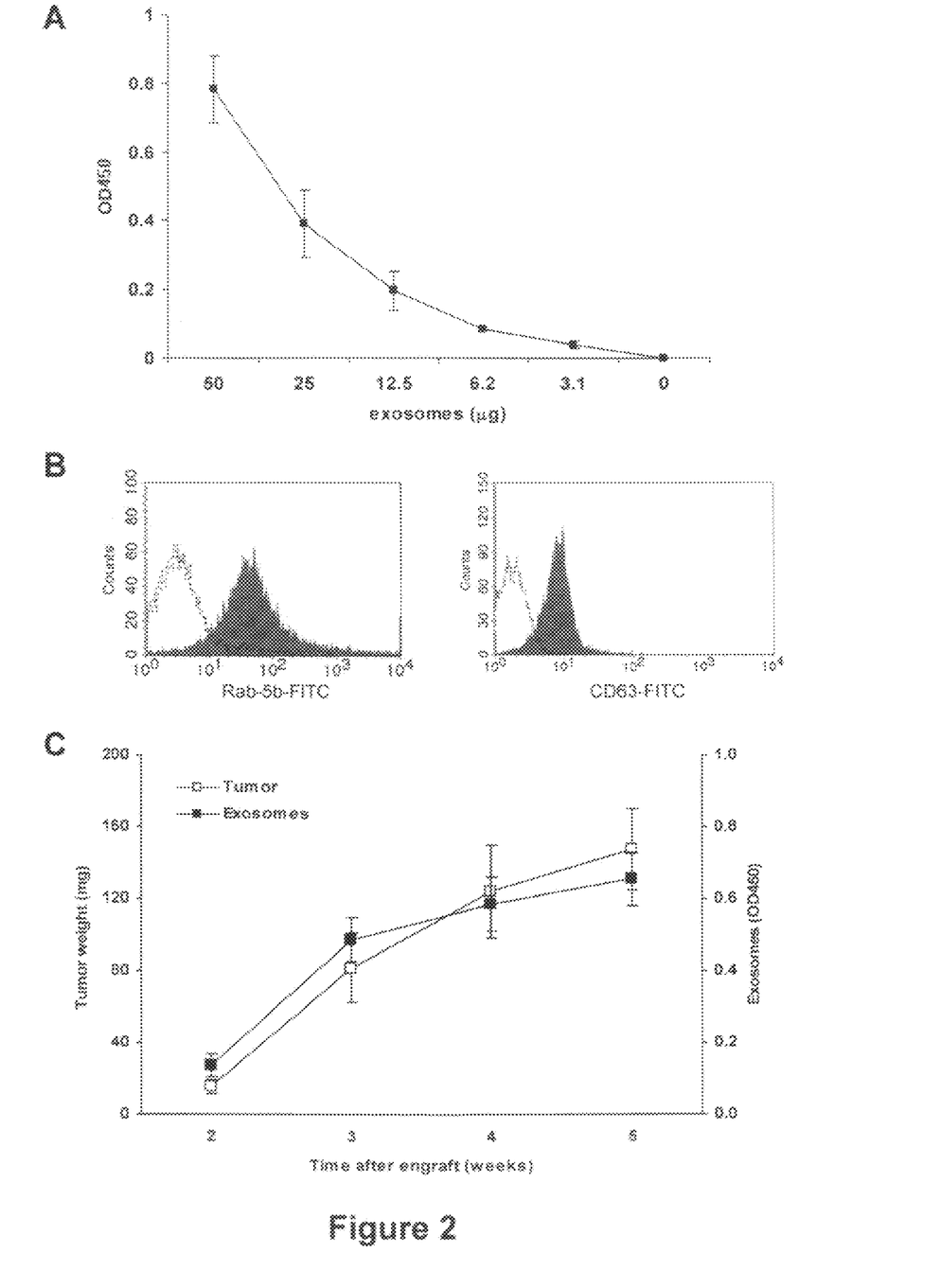
FIG. 2. Detection of Plasma Exosomes of SCID Mice Engrafted with Human Melanoma
  A. Dose-escalation analysis of tumor exosomes purified from plasma of SCID mice engrafted with human melanoma cells by ExoTest.
  B. FACS analysis of Rab-5b and CD63 expression in exosomes purified from plasma of SCID mice engrafted with human melanoma cells (Me501).
  C. Correlation of tumor size and levels of plasma exosomes in Me501-engrafted SCID mice analysed at different times during tumor growth. Groups of mice were represented by 5 animals for each time point. Exosome levels are expressed as OD450×1000.

Comparison of the Results of Qualification and Quantification of In Vivo Exosome Preparation of SCID Mice Engrafted with Human Tumors by FACs, WB and ExoTest In order to verify the possibility of detecting human tumor-derived exosomes in vivo by using ExoTest, we first performed experiments in which human melanoma (Me501) and colon carcinoma cell lines were injected subcutaneously in SCID mice. In the first experiments, plasma samples obtained at sacrifice from SCID mice carrying engrafted tumors (100-500 mg) were subjected to the exosome purification procedure. As for the exosomes purified from cell culture supernatants, also exosomes purified from mice plasma were clearly and specifically detectable by ExoTest (FIG. 2A) and FACS (FIG. 2B). Exosome preparations obtained from plasma of control SCID mice (not engrafted with human tumors) resulted in background optical densities comparable to the blank samples (OD=0.08±0.03), thus suggesting absence of exosomes in the immunocompromised animals or that murine exosomes do not cross react with human CD63 and Rab-5b. Again ExoTest needed a significantly smaller amount of exosome preparations to obtain results comparable to those using WB analysis.

After demonstrating that human exosomes can be recovered and detected by ExoTest, we performed time course experiments with the aim of evaluating whether the amount of plasma exosomes in human tumor-SCID mice correlated with tumor burden In these experiments, melanoma tumors were allowed to grow up to five weeks after the early engraftment, and the exosomes were purified and quantified from plasma of individual animals starting at day 14 after engraftment and during the following three weeks. The results showed that the amount of human exosomes detected by ExoTest increased over time in parallel to the increase of tumor size (FIG. 2C); suggesting that plasma exosome quantification represents a valuable method to monitor tumor growth. Similar results were obtained with MeBS cells (not shown).

Example 4

Tumor Exosomes Express Caveolin-1

Figure 3:
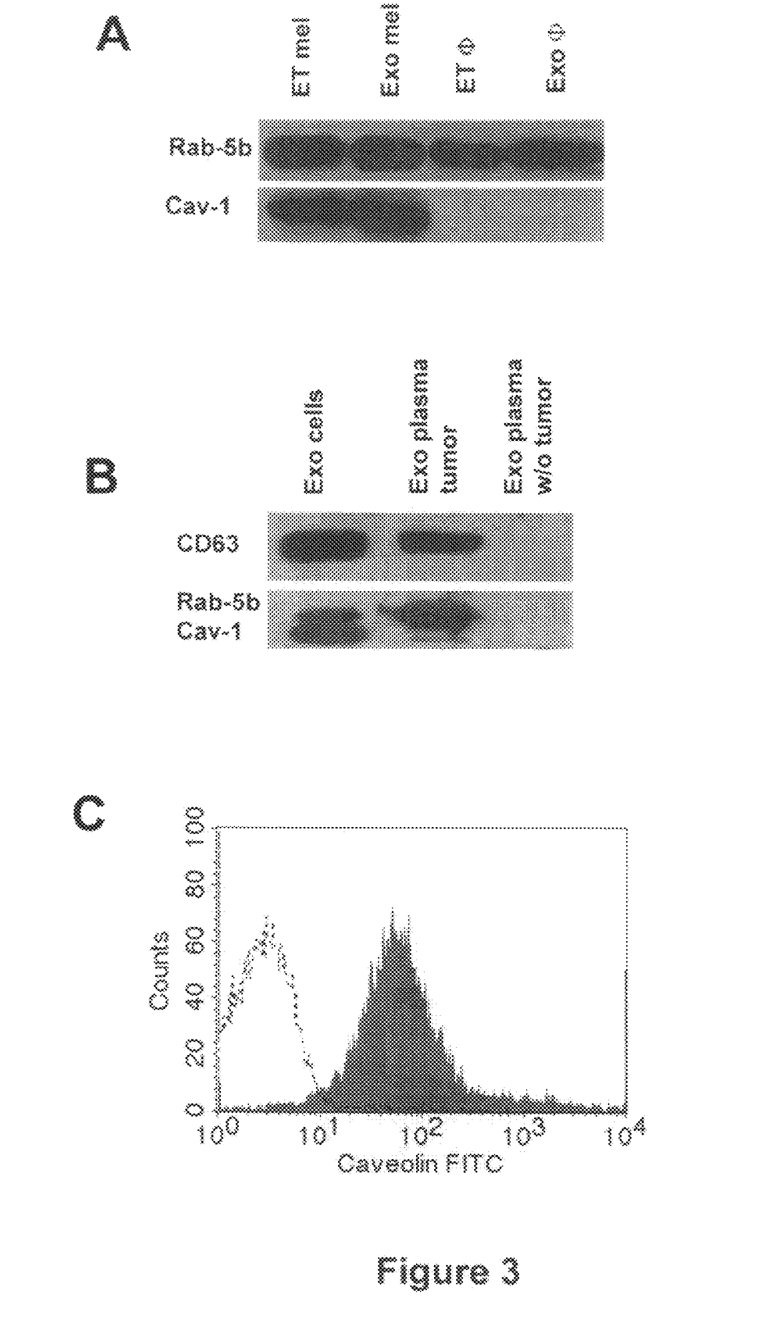
FIG. 3. Characterization of Caveolin-1 (Cav-1) Expression on Exosomes
  A. Western blot analysis of Cav-1 in cellular extracts and exosomes from human melanoma cells and macrophages.
  B. Western blot analysis of CD63, Rab-5b and Cav-1 in purified exosomes from Me501 cells, plasma of Me501-engrafted SCID mice and tumor-negative SCID mice.
  C. FACS analysis of Cav-1 expression on exosomes purified from plasma of Me501-engrafted SCID mice.

Since exosomes are known to represent an important and specific route of intercellular communication, we reasoned that tumor-derived exosomes may differ from circulating exosomes in normal physiological conditions. Recently, it has been reported that prostasomes (membrane vesicles secreted by prostate cancer cells) isolated from prostate carcinoma PC-3 cell line contain caveolin-1 protein, the major component of caveolae. It is also known that the serum levels of caveolin-1 are elevated in prostate cancer patients compared with healthy subjects (Tahir, 2003 #21). However, there is no prior art suggesting association of this protein with membrane vesicles in the blood. Therefore, we evaluated the presence of caveolin-1 on exosomes obtained from plasma of SCID mice engrafted with melanoma tumors. As is evidenced by results on FIG. 3A Cav1 is strongly expressed on exosomes secreted by human melanoma cells in vitro, while undetectable on both cellular extracts and exosomes from normal human cells such as for instance primary monocyte-derived macrophages (MDM). These results suggest that Ca1 secreted in an exosome-embedded form may be specific feature of melanoma cells, thus representing a potential marker for the ex-vivo analysis of tumor-derived exosomes. We therefore investigated the presence of Cav 1 on exosomes obtained from plasma of SCID mice engrafted with melanoma tumors. Cav 1 was detected in exosome preparations derived from plasma of SCID mice engrafted with melanoma tumors by Western blot (FIG. 3B), flow cytometry (FIG. 3C) and ExoTest, while Cav1 was undetectable in plasma-derived exosomes from control animals (FIG. 3B). In agreement with results from melanoma and colo-rectal carcinoma (CRC) patients other tumor markers, such as MelanA/Mart-1 for melanoma and CEA for CRC, could be used for detecting the in vivo release of tumor exosomes in tumor-bearing SCID mice by ExoTest, with results comparable with those obtained with Cav1. However, since melanoma may express heterogeneous or low amount of MelanA/MART-1, especially at metastatic levels, and CEA is present mostly in soluble form in CRC patients' serum, Cav1 is more reliable and reproducible tumor marker. Therefore, ExoTest is developed further with inclusion of anti-Cav1-specific antibodies.

Example 5

Quantification of In Vivo Exosome Preparation of Plasma of Tumor Patients by ExoTest: Amount of Exosomes in Plasma as a Tool to Prognosis The data obtained in the human tumor-SCID mouse model prompted us to investigate whether ExoTest allowed detection and characterization of exosomes purified from human plasma as well. If quatification was possible, we aimed to verify whether tumor patients may have circulating plasma exosomes that differ in quantity and/or quality from those present in plasma of healthy donors. Exosomes were purified from plasma of tumor patients (n=62) and healthy donors (n=37) and were then subjected to ExoTest and Western Blot analysis for the presence of Rab5 and CD63. Quantification of exosomes based on CD63 and Cav1 expression by ExoTest is shown in table 1.

TABLE 1

Plasma exosome and LDH levels in the study population.

| | CD63+ | Cav1+ exo | LDH |
|---|---|---|---|
| Melanoma patients | 478 | 524 | 438 |
| (n = 62) | (390 to 566) | (458 to 590) | (321 to 555) |
| Healthy donors | 236 | 213 | 360 |
| (n = 37) | (188 to 285) | (180 to 246) | (240 to 480) |

CD63+ and Cav1+ exo are plasmatic exosomes expressed as OD450 × 1000. Plasma LDH values are expressed as IU/L.
Data is shown as mean (95% C.I.)

Figure 4:
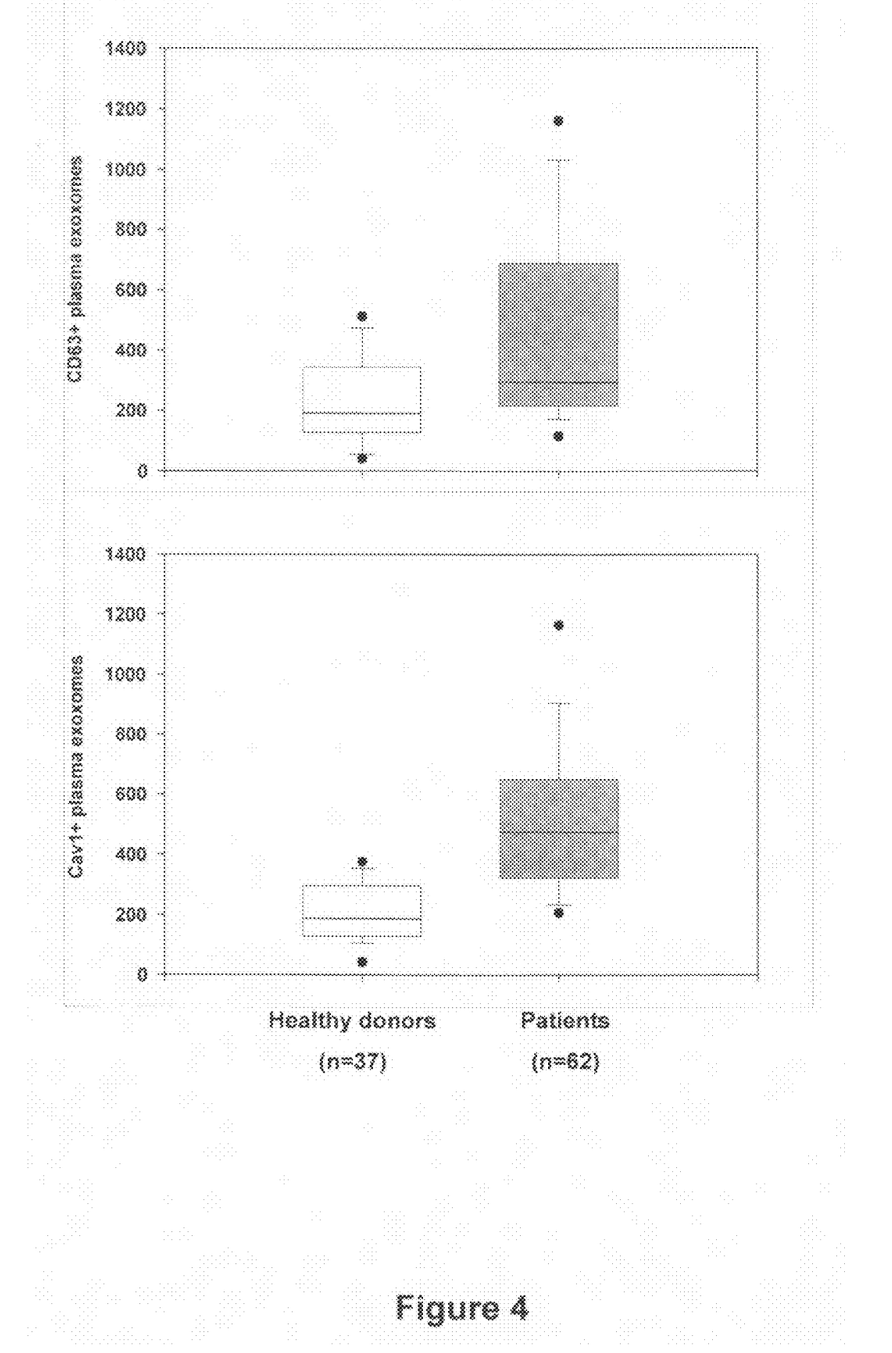
FIG. 4. Quantification of Exosomes in Plasma from Melanoma Patients

ExoTest test allowed the detection of exosomal proteins in plasma-purified exosomes from both melanoma patients and healthy donors (FIG. 4A), with up to 4 folds exosome levels in plasma of melanoma patients as compared to healthy donors (p<0.001). In order to determine sensitivity and specificity of ExoTest based on the detection of the two exosome protein markers, we calculated the cut-off (mean+/−2SD in healthy donors' samples) for both CD63 and Cav1 expressing plasma exosomes, which was 526 and 411 (OD450×1000), respectively. ExoTest detecting CD63+ exosomes showed a low sensitivity (36%) and good specificity (97.3%) while the ExoTest for Cav1+ exosomes had a higher sensitivity (62%) and similar specificity (97.3%). In line with this observation, the plasma levels of Cav1+ exosomes were significantly higher than the levels of CD63+ exosomes in melanoma patients (P=0.04). These results suggest that:
i) circulating Cav1 may be associated to exosomes in melanoma patients, and ii) quantification of plasma exosomes bearing Ca1 may be considered a useful tumor marker.

Figure 6:
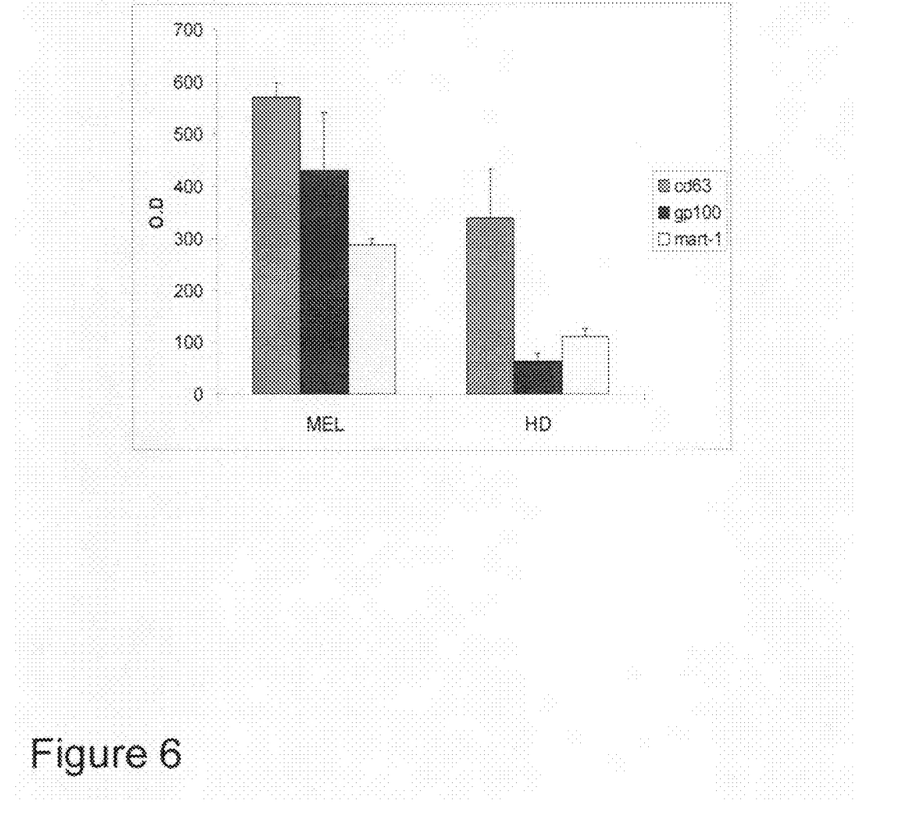
FIG. 6. Quantification of Exosomes in Plasma from Melanoma Patients.

In addition, we found that plasma LDH did not correlate with either CD63+ or Cav1+ plasma exosomes while a significant correlation was observed between CD63+ and Ca1+ plasma exosomes (Spearman coefficient 0.25, P=0.04) (FIG. 4). Moreover, ExoTest revealed the presence of tumor antigens, such as MART-1 or CEA in the plasma of carcinoma or melanoma patients (FIG. 6)

Most of the patients included into the analysis (57/62) were affected by advance disease (stage III-IV). A wide distribution of plasmatic exosome levels was detected by ExoTest in all disease stages, which suggest that the variability in the amount of exosomes present in peripheral circulation of different patients may reflect diverse levels of tumor aggressiveness and may therefore become a novel independent prognostic factor for melanoma. Other prognostic factors indicated by the American Joint Committee on Cancer (AJCC), including primary melanoma thickness and ulceration, number of metastatic lymph nodes, and site and number of distant metastases, also may correlate with exosomes serum content, as suggested by the results of this disclosure.

Example 6

Whole Plasma can be Used for Exosome Quantification

Figure 5:
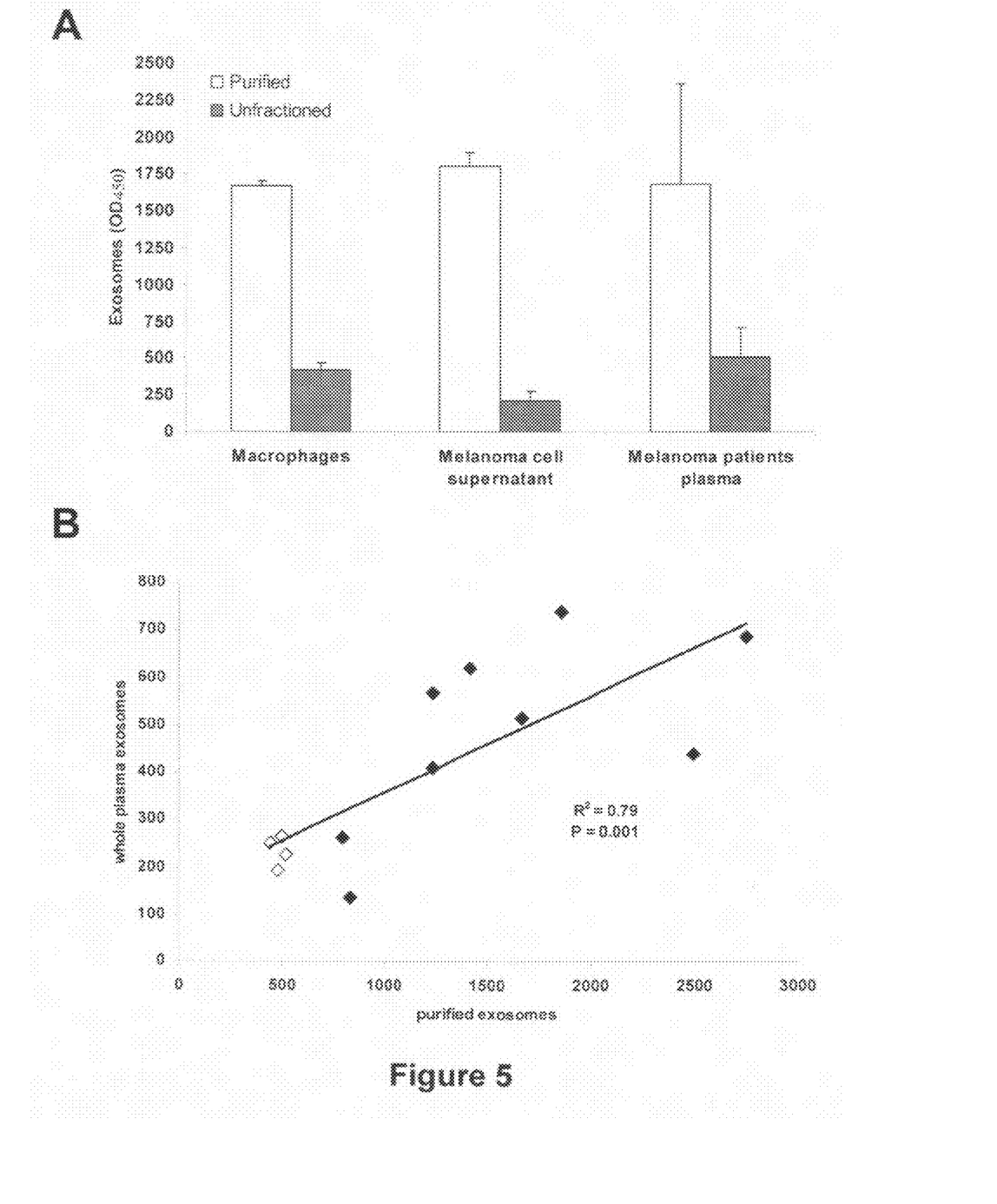
FIG. 5. ExoTest (ELISA) on Unfractioned Samples
  A. The amount of detectable exosomes was measured in purified exosomes (50 μg proteins) as compared to unfractioned culture supernatants (50 ml) from human macrophages, melanoma cells and plasma from melanoma patients. Data is expressed as means+/−SD.
  B. Regression analysis of plasma levels of CD63+ exosomes measured in purified or unfractioned plasma samples from both patients (n=9, black diamonds) and healthy donors (n=4, white diamonds). Exosome levels are expressed as OD450×1000.

The potential application of ExoTest for clinical purposes prompted us to verify whether ExoTest could be used for exosome detection in unfractionated biological fluids that would allow an easy and reproducible analysis avoiding the steps of ultracentrifugation. Therefore, we compared the detection and quantification of CD63+ exosomes from unfractionated samples (cell culture supernatants from human macrophages and melanoma cells, and human plasma) and exosomes purified from the same samples. In order to increase the sensitivity of the test, for these specific experiments the HRP-conjugated Mab was incubated for 30 minutes instead of 15 minutes. As is shown in FIG. 5A, the presence of exosomes from unfractioned macrophages and melanoma culture supernatants and plasma from nine melanoma patients was detectable by ExoTest. In addition, we performed the same analysis of plasma from 4 healthy donors and regression analysis on the total number of samples analysed (9 patients+4 healthy donors) showed a significant correlation between the two types of measures (FIG. 5B). These results suggest the potential application of ExoTest in clinical setting using whole plasma and avoiding the complex and time consuming procedures of exosome purification.

REFERENCES

Thery C, Zitvogel L, Amigorena S. Exosomes: composition, biogenesis and function. Nat Rev Immunol. 2002 August; 2(8):569-79.
Stoorvogel W, Kleijmeer M J, Geuze H J, Raposo G. The biogenesis and functions of exosomes. Traffic. 2002 May; 3(5):321-30.
Lamparski H G, Metha-Damani A, Yao J Y, Patel S, Hsu D H, Ruegg C, Le Pecq J B. Production and characterization of clinical grade exosomes derived from dendritic cells. J Immunol Methods. 2002 Dec. 15; 270(2):211-26.
Wubbolts R, Leckie R S, Veenhuizen P T, Schwarzmann G, Mobius W, Hoemschemeyer J, Slot J W, Geuze H J, Stoorvogel W. Proteomic and biochemical analyses of human B cell-derived exosomes. Potential implications for their function and multivesicular body formation. J Biol. Chem. 2003 Mar. 28; 278(13):10963-72.
Blanchard N, Lankar D, Faure F, Regnault A, Dumont C, Raposo G, Hivroz C. TCR activation of human T cells induces the production of exosomes bearing the TCR/CD3/zeta complex. J Immunol. 2002 Apr. 1; 168(7):3235-41
Raposo G, Tenza D, Mecheri S, Peronet R, Bonnerot C, Desaymard C. Accumulation of major histocompatibility complex class II molecules in mast cell secretory granules and their release upon degranulation. Mol Biol Cell. 1997 December; 8(12):2631-45.
van Niel G, Raposo G, Candalh C, Boussac M, Hershberg R, Cerf-Bensussan N, Heyman M. Intestinal epithelial cells secrete exosome-like vesicles. Gastroenterology. 2001 August; 121(2):337-49.
Andreola G, Rivoltini L, Castelli C, Huber V, Perego P, Deho P, et al. Induction of lymphocyte apoptosis by tumor cell secretion of FasL-bearing microvesicles. J Exp Med. 2002; 195(10):1303-1316.
Huber V, Fais S, Iero M, Lugini L, Canese P, Squarcina P, Zaccheddu A, Colone M, Arancia G, Gentile M, Seregni E, Valenti R, Ballabio G, Belli F, Leo E, Parmiani G, Rivoltini L. Human colorectal cancer cells induce T-cell death through release of proapoptotic microvesicles: role in immune escape. Gastroenterology. 2005 June; 128(7):1796-804.
Chaput N, Schartz N E, Andre F, Zitvogel L. Exosomes for immunotherapy of cancer. Adv Exp Med Biol. 2003; 532: 215-21.
Taylor D D, Taylor C G, Jiang C G, Black P H. Characterization of plasma membrane shedding from murine melanoma cells. Int J Cancer. 1988 Apr. 15; 41(4):629-35.
Taylor D D, Lyons K S, Gercel-Taylor C. Shed membrane fragment-associated markers for endometrial and ovarian cancers. Gynecol Oncol. 2002 March; 84(3):443-8.
Ginestra A, La Placa M D, Saladino F, Cassara D, Nagase H, Vittorelli M L. The amount and proteolytic content of vesicles shed by human cancer cell lines correlates with their in vitro invasiveness. Anticancer Res. 1998 September-October; 18(5A):3433-7.
Admyre C, Grunewald J, Thyberg J, Gripenback S, Tornling G, Eklund A, Scheynius A, Gabrielsson S. Exosomes with major histocompatibility complex class II and co-stimulatory molecules are present in human BAL fluid. Eur Respir J. 2003 October; 22(4):578-83.
Andre F, Schartz N E, Movassagh M, Flament C, Pautier P, Morice P, Pomel C, Lhomme C, Escudier B, Le Chevalier T, Tursz T, Amigorena S, Raposo G, Angevin E, Zitvogel L. Malignant effusions and immunogenic tumour-derived exosomes. Lancet. 2002 Jul. 27; 360(9329):295-305.
Bard M P, Hegmans J P, Hemmes A, Luider T M, Willemsen R, Severijnen L A, van Meerbeeck J P, Burgers S A, Hoogsteden H C, Lambrecht B N. Proteomic analysis of exosomes isolated from human malignant pleural effusions. Am J Respir Cell Mol Biol. 2004 July; 31(1):114-21.
Caby M P, Lankar D, Vincendeau-Scherrer C, Raposo G, Bonnerot C. Exosomal-like vesicles are present in human blood plasma. Int Immunol. 2005 July; 17(7):879-87.
Hegmans J P, Bard M P, Hemmes A, Luider T M, Kleijmeer M J, Prins J B, Zitvogel L, Burgers S A, Hoogsteden H C, Lambrecht B N. Proteomic analysis of exosomes secreted by human mesothelioma cells. Am J Pathol. 2004 May; 164(5):1807-15.
Laulagnier K, Motta C, Hamdi S, Roy S, Fauvelle F, Pageaux J F, Kobayashi T, Salles J P, Perret B, Bonnerot C, Record M. Mast cell- and dendritic cell-derived exosomes display a specific lipid composition and an unusual membrane organization. Biochem J. 2004 May 15; 380(Pt 1):161-71.
Clayton A, Turkes A, Dewitt S, Steadman R, Mason M D, Hallett M B. Adhesion and signaling by B cell-derived exosomes: the role of integrins. FASEB J. 2004 April
de Gassart A, Geminard C, Fevrier B, Raposo G, Vidal M. Lipid raft-associated protein sorting in exosomes. Blood. 2003 Dec. 15; 102(13):4336-44.
Mobius W, van Donselaar E, Ohno-Iwashita Y, Shimada Y, Heijnen H F, Slot J W, Geuze H J. Recycling compartments and the internal vesicles of multivesicular bodies harbor most of the cholesterol found in the endocytic pathway. Traffic. 2003 April; 4(4):222-31.
Schartz N E, Chaput N, Andre F, Zitvogel L. From the antigen-presenting cell to the antigen-presenting vesicle: the exosomes. Curr Opin Mol Ther. 2002 August; 4(4):372-81.

Chaput N, Taieb J, Schartz N E, Andre F, Angevin E, Zitvogel L. Exosome-based immunotherapy. Cancer Immunol Immunother. 2004 March; 53(3):234-9.

Nguyen D G, Booth A, Gould S J, Hildreth J E. Evidence that HIV budding in primary macrophages occurs through the exosome release pathway. J Biol Chem. 2003 Dec. 26; 278(52):52347-54. Blood. 2003 Dec. 15; 102(13):4336-44.

Flanagan J, Middeldorp J, Sculley T. Localization of the Epstein-Barr virus protein LMP 1 to exosomes. J Gen Virol. 2003 July; 84(Pt 7):1871-9.

Raposo G, Nijman H W, Stoorvogel W, Liejendekker R, Harding C V, Melief C J, Geuze H J. B lymphocytes secrete antigen-presenting vesicles. J Exp Med. 1996 Mar. 1; 183 (3):1161-72.

Zitvogel L, Regnault A, Lozier A, Wolfers J, Flament C, Tenza D, Ricciardi-Castagnoli P, Raposo G, Amigorena S. Eradication of established murine tumors using a novel cell-free vaccine: dendritic cell-derived exosomes. Nat Med. 1998 May; 4(5):594-600.

Smith T J, Weis J H. Mucosal T cells and mast cells share common adhesion receptors. Immunol Today. 1996 February; 17(2):60-3. Review.

Lozupone F, Luciani F, Venditti M, Rivoltini L, Pupa S, Parmiani G, et al. Murine granulocytes control human tumor growth in SCID mice. Int J. Cancer. 2000; 87:569-573.

Lozupone F, Pende D, Burgio V L, Castelli C, Spada M, Venditti M, et al. Adoptive transfer of an anti-MART-$1_{27-35}$-specific CD8$^+$ T cell clone leads to immunoselection of human melanoma antigen-loss variants in SCID mice. Eur J. Immunol. 2003; 33:556-566.

Tahir S A, Yang G, Ebara S, Timme T L, Satoh T, Li 20.L, Goltsov A, Ittmann M, Morrisett J D, Thompson T C. Secreted caveolin-1 stimulates cell survival/clonal growth and contributes to metastasis in androgen-insensitive prostate cancer. Cancer Res. 2001 May 15; 61(10):3882-5.

Mouraviev V, Li L, Tahir S A, Yang G, Timme T M, Goltsov A, Ren C, Satoh T, Wheeler T M, Ittmann M M, Miles B J, Amato R J, Kadmon D, Thompson T C. The role of caveolin-1 in androgen insensitive prostate cancer. J Urol. 2002 October; 168(4 Pt 1):1589-96.

D D Taylor and C Gergel-Taylor Tumour-derived exosomes and their role in cancer-associated T-cell signalling defects British Journal of Cancer (2005) 92, 305311

What is claimed is:

1. A method to quantify and qualify tumor-related exosomes in unfractionated human body fluid samples, said method having the steps consisting of:
    a) capturing total exosomes of the body fluid sample with a primary antibody Rab-5;
    b) detecting tumor-related exosomes from the captured total exosomes with a detection antibody;
    c) allowing an enzyme linked secondary antibody to react with the detection antibody;
    d) adding substrate; and
    e) detecting the reaction.

2. The method of claim 1, wherein the body fluid is unfractionated sample of human plasma, ascites, cerebral fluids, bone marrow, urine, faeces or bronco-alveolar washing.

3. The method of claim 2, wherein volume of the body fluid used is less than 2 ml.

4. The method of claim 1, wherein the primary antibody is anti-Rab5b antibody.

5. A non-invasive method to monitor tumor growth, said method having the steps consisting of:
    a) periodically taking a body fluid sample of a patient;
    b) capturing total exosomes of the sample with a primary antibody anti-Rab 5;
    c) detecting tumor related exosomes from the captured total exosomes with a detection antibody;
    d) allowing an enzyme linked secondary antibody to react with the detection antibody;
    e) adding substrate;
    f) detecting the reaction; and
    g) drawing a correlation between quantity of detected exosomes and size of the tumor.

6. The method of claim 5, wherein the primary antibody is anti-Rab 5b antibody and the detection antibody is anti-CD63 or anti-caveolin-1.

7. The method of claim 5, wherein the tumor is melanoma tumor.

8. A method to diagnose a tumor, by detecting caveolin-1 bearing exosomes by using method of claim 1, wherein the detecting antibody is anti-caveolin-1.

9. The method of claim 8, wherein the tumor is melanoma tumor.

10. The method of claim 4, wherein the detection antibody is against a tumor specific protein.

11. The method of claim 10, wherein the detection antibody is anti-CD63 or anti-caveolin-1.

12. The method of claim 1, wherein the body fluid sample is received from a healthy person and from a patient suspected to have a tumor, and the detected quantity of exosomes in patient's sample is compared to the quantity of exosomes in the healthy person's sample, and an increase in the quantity is used as indication of a tumor.

13. The method of claim 5, wherein the body fluid sample is received from a healthy person and from a patient suspected to have a tumor, and the detected quantity of exosomes in patient's sample is compared to the quantity of exosomes in the healthy person's sample, and an increase in the quantity is used as indication of melanoma tumors.

14. A method to quantify and qualify tumor related exosomes in a human body fluid sample, said method having the steps consisting of:
    a) optionally purifying an exosome preparation from the human body fluid sample;
    b) capturing total exosomes of the optionally purified exosome preparation or body fluid sample with primary antibody, said primary antibody being anti-Rab 5b;
    c) detecting tumor related exosomes from the bound exosomes with a detection antibody, said detection antibody being anti-caveolin-1;
    d) allowing an enzyme linked secondary antibody to react with the detection antibody;
    e) adding substrate; and
    f) detecting the reaction.

15. A method to quantify and characterize tumor-related exosomes in an unfractionated human body fluid sample, said method comprising the steps of:
    a) capturing total exosomes from the body fluid sample of about 2 ml or less in volume on an ELISA-plate coated with an anti-Rab5b antibody;
    b) detecting tumor-related exosomes from the captured total exosomes with a detection antibody, said detection antibody being anti-caveolin-1;
    c) allowing an enzyme linked secondary antibody to react with the detection antibody;
    d) adding substrate; and
    e) detecting the reaction.

* * * * *